(12) United States Patent
Maeda et al.

(10) Patent No.: US 9,174,899 B2
(45) Date of Patent: Nov. 3, 2015

(54) METHOD FOR PRODUCING OPTICALLY ACTIVE ALCOHOLS

(71) Applicant: HAMARI CHEMICALS, LTD., Osaka (JP)

(72) Inventors: Sadayuki Maeda, Kyoto (JP); Tatsunori Sato, Hyogo (JP)

(73) Assignee: HAMARI CHEMICALS, LTD., Osaka (JP)

( * ) Notice: Subject to any disclaimer, the term of this patent is extended or adjusted under 35 U.S.C. 154(b) by 0 days.

(21) Appl. No.: 14/353,484

(22) PCT Filed: Oct. 24, 2012

(86) PCT No.: PCT/JP2012/077464
§ 371 (c)(1),
(2) Date: Apr. 22, 2014

(87) PCT Pub. No.: WO2013/061999
PCT Pub. Date: May 2, 2013

(65) Prior Publication Data
US 2014/0296584 A1    Oct. 2, 2014

(30) Foreign Application Priority Data

Oct. 25, 2011   (JP) .............................. 2011-234421

(51) Int. Cl.
| | | |
|---|---|---|
| C07D 207/09 | (2006.01) | |
| C07C 29/143 | (2006.01) | |
| C07D 311/74 | (2006.01) | |
| C07C 41/26 | (2006.01) | |
| C07B 53/00 | (2006.01) | |

(52) U.S. Cl.
CPC .............. *C07C 29/143* (2013.01); *C07B 53/00* (2013.01); *C07C 41/26* (2013.01); *C07D 207/09* (2013.01); *C07D 311/74* (2013.01); *C07B 2200/07* (2013.01); *C07C 2102/10* (2013.01)

(58) Field of Classification Search
CPC .................................................... C07D 207/09
USPC .......................................... 548/572; 568/881
See application file for complete search history.

(56) References Cited

U.S. PATENT DOCUMENTS 6,184,381 B1    2/2001   Ikariya et al.
2003/0120088 A1   6/2003   Senda et al.

FOREIGN PATENT DOCUMENTS

| JP | H09157196 A | 6/1997 |
|---|---|---|
| JP | 2003176266 A | 6/2003 |
| WO | WO-02/10101 A1 * | 2/2002 |

OTHER PUBLICATIONS

Ahlford et al., "Amino acid derived amides and hydroxamic acids as ligands for asymmetric transfer hydrogenation in aqueous media," Catalysis Communications, vol. 12, pp. 1118-1121 (2011).*
Manville et al., "Application of Proline-Functionalised 1,2-Diphenylethane-1,2-diamine (DPEN) in Asymmetric Transfer Hydrogenation of Ketones," Eur. J. Org. Chem., .6893-6901 (2011).*
International Preliminary Report on Patentability in corresponding PCT/JP2012/077464 dated Jul. 8, 2014. (English Translation).
Xie et al., "Highly Enantioselective Hydrogenation of α-Arylmethylene Cycloalkanones Catalyzed by Iridium Complexes of Chiral Spiro Aminophosphine Ligands," *J. Am. Chem. Soc.*, vol. 132, pp. 4538-4539 (2010).
International Search Report in corresponding PCT/JP2012/077464 dated Dec. 11, 2012.
Written Opinion in corresponding PCT/JP2012/077464 dated Dec. 11, 2012.
Manville et al., "Application of Proline-Functionalised 1,2-Diphenylethane-1,2-diamine (DPEN) in Asymmetric Transfer Hydrogenation of Ketones," *Eur. J. Org. Chem.*, pp. 6893-6901 (2011).

(Continued)

*Primary Examiner* — Kamal Saeed
*Assistant Examiner* — Janet L Coppins
(74) *Attorney, Agent, or Firm* — Marshall, Gerstein & Borun LLP

(57) ABSTRACT

A method is provided for producing optically active alcohols from ketones by reducing a ketone in the presence of an iridium(III) complex having a chiral prolinamide compound as a ligand. The ketone is preferably a compound represented by formula [I]:

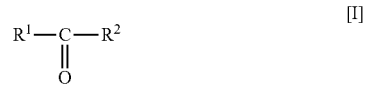

(wherein $R^1$ and $R^2$ are different from each other, and each represent an optionally substituted straight or branched alkyl group, an optionally substituted cycloalkyl group, an optionally substituted aryl group, an optionally substituted heteroaryl group, an optionally substituted aralkyl group, an optionally substituted heteroarylalkyl group, an optionally substituted alkenyl group or an optionally substituted alkynyl group, and $R^1$ and $R^2$ may be bound to each other at any appropriate position to form a ring, the ring optionally containing one or more atoms which may be the same or different and are selected from an oxygen atom, an optionally substituted nitrogen atom and a sulfur atom, and optionally being condensed with an aromatic or hetero-aromatic ring).

25 Claims, No Drawings

(56) References Cited

OTHER PUBLICATIONS

Faller et al., "Catalysts for the Asymmetric Transfer Hydrogenation of Ketones Derived from L-Prolinamide and (p-CymeneRuCl$_2$)$_2$ or Cp*RhCl$_2$)$_2$," *Organometallics*, vol. 20, pp. 5245-5247 (2001).

Yoon Rhyoo et al., "Use of amino amides derived from proline as chiral ligands in the ruthenium(II)-catalyzed transfer hydrogenation reaction of ketones," *Tetrahedron Letters*, vol. 42, pp. 5045-5048 (2001).

Maeda et al., "Development of highly efficient "simple" catalysts for asymmetric transfer hydrogenation and their application to the synthesis of chiral pharmaceuticals," *The Japanese Society for Process Chemistry 2012 Summer Symposium (Kyoto)*, pp. 276-277, 2P-45 (Jun. 25, 2012).

Mogi et al., "Asymmetric reduction of methoxy substituted β-tetralones using transfer hydrogenation," *Tetrahedron: Asymmetry*, vol. 15, pp. 3715-3717 (2004).

* cited by examiner

METHOD FOR PRODUCING OPTICALLY ACTIVE ALCOHOLS

TECHNICAL FIELD

The present invention relates to a novel method for producing optically active alcohols.

BACKGROUND ART

Optically active alcohols are compounds of great importance used as a synthetic raw material for the production of pharmaceuticals, agrochemicals, liquid crystal materials, fine chemicals, etc.

Among various methods for producing optically active alcohols, the most efficient is a method involving catalytic asymmetric reduction of unsymmetrical ketones, and so far a lot of catalysts for asymmetric reduction of ketones have been developed. In particular, asymmetric transfer hydrogenation using RuCl(Tsdpen)(p-cymene) or other chiral ruthenium complexes having an optically active diamine ligand, which was invented by Noyori et al. (see Patent Literature 1, for example), is the most industrially advantageous method. The reasons for this are that the product can be obtained in very high enantiomeric excess, and that organic compounds such as 2-propanol and formic acid can be used as a hydrogen source without the need of such specialized equipment as required in the case where high-pressure hydrogen gas is used as a reducing agent.

Asymmetric reduction using, as a catalyst, a complex of a transition metal, such as rhodium, ruthenium and iridium, with an optically active ligand Tsdpen (N-(2-amino-1,2-diphenylethyl)-p-toluenesulfonamide) is a conventionally well-known method, but Tsdpen is so expensive a compound as to prevent the industrial application of this reaction. This method produces optically active alcohols in good enantiomeric excess from ketones in which a carbonyl group is bound directly to an aromatic ring, but in cases where ketones in which a carbonyl group is bound to an aromatic ring via a methylene group, for example β-tetralone, are used as a starting material, the method has the serious drawback of greatly reducing the enantiomeric excess of the product (see Non Patent Literature 1, for example). For those reasons, this conventional method is not versatile and there is a pressing need for methods for industrially producing optically active alcohols.

CITATION LIST

Patent Literature

Patent Literature 1: JP-A 9-157196

Non Patent Literature

Non Patent Literature 1: Tetrahedron Asymmetry, 2004, 15, 3715-3717

SUMMARY OF INVENTION

Technical Problem

The present invention overcomes the above-mentioned problems by providing an industrially advantageous method for producing optically active alcohols in high yields from ketones of various structures by using an inexpensive chiral catalyst.

Solution to Problem

The present inventors already filed a patent application claiming an iridium(III) complex having a chiral prolinamide compound as a ligand, the complex being capable of serving as a very good catalyst for asymmetric reduction of imines (see Japanese Patent Application No. 2007-175278). The present inventors attempted to obtain optically active alcohols by asymmetric reduction of ketones using this catalyst, and found the surprising results that, regardless of the structure of starting material ketones, optically active alcohols are generally obtainable in high enantiomeric excess. Then, the present inventors completed the present invention.

That is, the present invention includes the following.

[1] A method for producing optically active alcohols, comprising reducing a ketone in the presence of an iridium(III) complex having a chiral prolinamide compound as a ligand.

[2] The method according to the above [1], wherein the ketone is a compound represented by formula [I]:

[I]

(wherein $R^1$ and $R^2$ are different from each other, and each represent an optionally substituted straight or branched alkyl group, an optionally substituted cycloalkyl group, an optionally substituted aryl group, an optionally substituted heteroaryl group, an optionally substituted aralkyl group, an optionally substituted heteroarylalkyl group, an optionally substituted alkenyl group or an optionally substituted alkynyl group, and $R^1$ and $R^2$ may be bound to each other at any appropriate position to form a ring, the ring optionally containing one or more atoms which may be the same or different and are selected from an oxygen atom, an optionally substituted nitrogen atom and a sulfur atom).

[3] The method according to the above [2], wherein the ring is a condensed ring of an optionally substituted aliphatic carbocyclic or heterocyclic ring and an optionally substituted aromatic or hetero-aromatic ring.

[4] The method according to any one of the above [1] to [3], wherein the optically active alcohol is a compound represented by formula [II]:

[II]

(wherein $R^1$ and $R^2$ are as defined in formula [I], and the symbol * indicates that the carbon atom is a chiral center).

[5] The method according to any one of the above [1] to [4], wherein the chiral prolinamide compound is a compound represented by formula [III]:

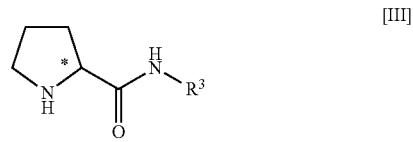

[III]

(wherein $R^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol * indicates that the carbon atom is a chiral center).

[6] The method according to any one of the above [1] to [5], wherein the chiral prolinamide compound is (R)-proline heteroaryl amide or (S)-proline heteroaryl amide.

[7] The method according to any one of the above [1] to [6], wherein the chiral prolinamide compound is (R)—N-(6-quinolinyl)-2-pyrrolidinecarboxamide or (S)—N-(6-quinolinyl)-2-pyrrolidinecarboxamide.

[8] The method according to any one of the above [1] to [6], wherein the chiral prolinamide compound is (R)—N-(2-methoxy-3-dibenzofuranyl)-2-pyrrolidinecarboxamide or (S)—N-(2-methoxy-3-dibenzofuranyl)-2-pyrrolidinecarboxamide.

[9] The method according to any one of the above [1] to [5], wherein the chiral prolinamide compound is (R)-2-pyrrolidinecarboxamide or (S)-2-pyrrolidinecarboxamide.

[10] The method according to any one of the above [1] to [6], wherein the iridium(III) complex having a chiral prolinamide compound as a ligand is an (R)- or (S)-chloro[(1,2,3,4,5-η)-pentamethyl-2,4-cyclopentadien-1-yl] [N-(2-methoxy-3-dibenzofuranyl)-2-pyrrolidinecarboxamidato-κN1, κN2]iridium(III) catalyst, or an (R)- or (S)-chloro[(1,2,3,4,5-η)-pentamethyl-2,4-cyclopentadien-1-yl] (N-6-quinolinyl-2-pyrrolidinecarboxamidato-κN1, κN2)iridium(III) catalyst.

[11] The method according to any one of the above [1] to [5] and [9], wherein the iridium(III) complex having a chiral prolinamide compound as a ligand is an (R)- or (S)-chloro [(1,2,3,4,5-η)-pentamethyl-2,4-cyclopentadien-1-yl] (2-pyrrolidinecarboxamidato-κN1,κN2)iridium(III) catalyst.

[12] The method according to any one of the above [1] to [11], wherein the iridium(III) complex having a chiral prolinamide compound as a ligand is crystalline.

[13] The method according to any one of the above [1] to [12], wherein the ketone is reduced by reacting with a hydrogen donor compound.

[14] The method according to the above [13], wherein the hydrogen donor compound is formic acid or a salt thereof.

Advantageous Effects of Invention

According to the present invention, ordinary ketones can be used without any structural limitation as a starting material for the production of optically active alcohols, and a wide variety of optically active alcohols can be provided in high optical and chemical purities with the use of the starting material and an inexpensive complex catalyst.

In more detail, the ligand of a conventional catalyst for an asymmetric reaction is a metal complex having a complicated structure and very expensive, whereas the ligand used for the present invention is a chiral prolinamide compound having a simple structure. Particularly, (R)- and (S)-prolinamides have a low molecular weight and are readily industrially producible as an inexpensive compound, and therefore, the production method of the present invention is of great value in industrial use.

DESCRIPTION OF EMBODIMENTS

Hereinafter, the present invention will be explained in detail.

The method of the present invention for producing optically active alcohols comprises reducing a ketone in the presence of an iridium(III) complex having a chiral prolinamide compound as a ligand.

The production method of the present invention can be conducted according to, for example, the reaction formula shown below.

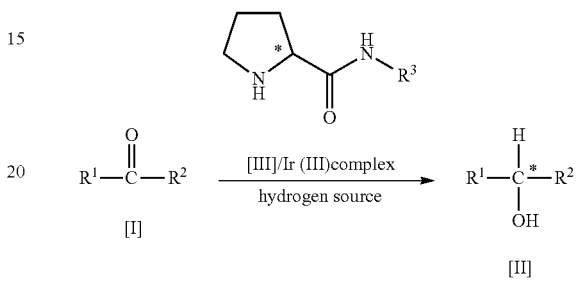

<Starting Material>

The ketone used as the starting material in the production method of the present invention is not particularly limited, may be any compound having a ketone group in a molecule, and is appropriately selected depending on desired optically active alcohols.

The ketone used as the starting material in the production method of the present invention is preferably a compound represented by formula [I]:

(wherein $R^1$ and $R^2$ are different from each other, and each represent an optionally substituted straight or branched alkyl group, an optionally substituted cycloalkyl group, an optionally substituted aryl group, an optionally substituted heteroaryl group, an optionally substituted aralkyl group, an optionally substituted heteroarylalkyl group, an optionally substituted alkenyl group or an optionally substituted alkynyl group, and $R^1$ and $R^2$ may be bound to each other at any appropriate position to form a ring, the ring optionally containing one or more atoms which may be the same or different and are selected from an oxygen atom, an optionally substituted nitrogen atom and a sulfur atom, and optionally being a condensed ring of an optionally substituted aliphatic carbocyclic or heterocyclic ring and an optionally substituted aromatic or hetero-aromatic ring).

The "straight or branched alkyl group" in the optionally substituted straight or branched alkyl group represented by $R^1$ and $R^2$ is, for example, a straight or branched alkyl group having 1 to 20 carbon atoms. The specific examples include a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, a nonyl group, a decyl group, a dodecyl group, a pentadecyl group, a hexadecyl group and an octadecyl group.

The "cycloalkyl group" in the optionally substituted cycloalkyl group represented by $R^1$ and $R^2$ is, for example, a cycloalkyl group having 3 to 20 carbon atoms. The specific examples include a cyclopropyl group, a cyclobutyl group, a cyclopentyl group, a cyclohexyl group and a cycloheptyl group.

The "aryl group" in the optionally substituted aryl group represented by $R^1$ and $R^2$ is, for example, an aryl group having 6 to 20 carbon atoms. The specific examples include a phenyl group, a 1-naphthyl group, a 2-naphthyl group, an anthryl group, a phenanthryl group, a 2-biphenyl group, a 3-biphenyl group, a 4-biphenyl group and a terphenyl group.

The "heteroaryl group" in the optionally substituted heteroaryl group represented by $R^1$ and $R^2$ is, for example, a heteroaryl group having a heteroatom selected from a nitrogen atom, a sulfur atom, an oxygen atom and the like. The specific examples include a furanyl group, a thienyl group, an oxazolyl group, an isoxazolyl group, a thiazolyl group, an isothiazolyl group, a pyrrolyl group, an imidazolyl group, a pyrazolyl group, a pyridyl group, a pyrimidinyl group, a pyrazinyl group, a phthalazinyl group, a triazinyl group, an indolyl group, an isoindolyl group, a quinolinyl group, an isoquinolinyl group and a dibenzofuranyl group.

The "aralkyl group" in the optionally substituted aralkyl group represented by $R^1$ and $R^2$ is, for example, a group which is the same as the above-defined alkyl group except for having an aryl group instead of a hydrogen atom. The specific examples include a benzyl group, a phenylethyl group and a phenylpropyl group.

The "heteroaryl group" in the optionally substituted heteroarylalkyl group represented by $R^1$ and $R^2$ is, for example, a heteroaryl group having a heteroatom selected from a nitrogen atom, a sulfur atom, an oxygen atom and the like. The specific examples include a furanyl group, a thienyl group, an oxazolyl group, an isoxazolyl group, a thiazolyl group, an isothiazolyl group, a pyrrolyl group, an imidazolyl group, a pyrazolyl group, a pyridyl group, a pyrimidinyl group, a pyrazinyl group, a phthalazinyl group, a triazinyl group, an indolyl group, an isoindolyl group, a quinolinyl group, an isoquinolinyl group and a dibenzofuranyl group.

The "alkenyl group" in the optionally substituted alkenyl group represented by $R^1$ and $R^2$ is, for example, an alkenyl group having 2 to 20 carbon atoms. The specific examples include a vinyl group, an allyl group, a butenyl group and a hexenyl group.

The "alkynyl group" in the optionally substituted alkynyl group represented by $R^1$ and $R^2$ is, for example, an alkynyl group having 2 to 20 carbon atoms. The specific examples include an ethynyl group and a propynyl group.

The substituting group (substituent) in the above "straight or branched alkyl group," "cycloalkyl group," "aryl group," "heteroaryl group," "aralkyl group," "heteroarylalkyl group," "alkenyl group" and "alkynyl group" may be of any kind unless the substituting group adversely affects the reaction, and the examples include halogen atoms (for example, a fluorine atom, a chlorine atom, a bromine atom, an iodine atom, etc.), straight or branched alkyl groups (for example, a methyl group, an ethyl group, a propyl group, an isopropyl group, a butyl group, an isobutyl group, a tert-butyl group, a pentyl group, a hexyl group, etc.), aralkyl groups (for example, a phenylethyl group, a phenylpropyl group, a naphthylmethyl group, etc.), straight or branched alkoxy groups (for example, a methoxy group, an ethoxy group, a propoxy group, an isopropoxy group, a butoxy group, an isobutoxy group, a tert-butoxy group, a pentyloxy group, etc.), haloalkyl groups (for example, a trifluoromethyl group, a trichloromethyl group, etc.), haloalkoxy groups (for example, a fluoromethoxy group, a difluoromethoxy group, a trifluoromethoxy group, a trifluoroethoxy group, a tetrafluoroethoxy group, etc.), a hydroxyl group, a protected hydroxyl group (examples of the protecting group for a hydroxyl group include an acetyl group, a benzoyl group, a methoxymethyl group, a tetrahydropyranyl group, a trimethylsilyl group, a tert-butyldimethylsilyl group and a carbonate ester group), an amino group, a protected amino group (examples of the protecting group for an amino group include a formyl group, an acetyl group, a benzoyl group, a benzyloxycarbonyl group, a phthaloyl group, a carbamoyl group and a ureido group), an arylamino group, a heteroarylamino group, a mercapto group, a nitro group, a nitrile group, a carboxyl group and an alkoxycarbonyl group. Hereinafter, the substituting group (substituent) of this kind is called substituting group (A) in some cases.

The number of the substituting groups in the "straight or branched alkyl group," "cycloalkyl group," "aryl group," "heteroaryl group," "aralkyl group," "heteroarylalkyl group," "alkenyl group" and "alkynyl group" can be 1 to 4, for example.

The "straight or branched alkyl group," "cycloalkyl group," "aryl group," "heteroaryl group," "aralkyl group," "heteroarylalkyl group," "alkenyl group" and "alkynyl group" may contain one or more atoms which may be the same or different and are selected from an oxygen atom, an optionally substituted nitrogen atom and a sulfur atom. Examples of the substituting group in the optionally substituted nitrogen atom are the same as those of the substituting group in the "straight or branched alkyl group" described above.

In the compounds of formulae [I] and [III], $R^1$ and $R^2$ may be bound to each other at any appropriate position to form a ring. Thus, in the present invention, it is optional whether $R^1$ and $R^2$ together with the adjacent carbon atom form a ring or not, but it is preferred that such a ring is formed.

The ring may be a monocyclic or polycyclic ring system. In the case where the ring is a polycyclic ring system, the ring may be a polycyclic or condensed ring consisting of two or more monocyclic rings. In the case where the ring is a polycyclic ring system, the ring may be a polycyclic or condensed ring consisting of two or more aliphatic carbocyclic or heterocyclic rings, or a polycyclic or condensed ring consisting of an aliphatic carbocyclic or heterocyclic ring and an aromatic or hetero-aromatic ring.

The ring may contain one or more atoms which may be the same or different and are selected from an oxygen atom, an optionally substituted nitrogen atom and a sulfur atom. Examples of the substituting group in the optionally substituted nitrogen atom are the same as those of the substituting group in the "straight or branched alkyl group" described above.

The ring is preferably a condensed ring of an optionally substituted aliphatic carbocyclic or heterocyclic ring and an optionally substituted aromatic or hetero-aromatic ring.

The "aliphatic carbocyclic ring" in the optionally substituted aliphatic carbocyclic ring is, for example, a 4 to 10-membered aliphatic carbocyclic ring. The specific examples include cyclopropane, cyclobutane, cyclopentane, cyclohexane, cycloheptane, cyclooctane, cyclononane and cyclodecane.

The "heterocyclic ring" in the optionally substituted heterocyclic ring is, for example, a 4- to 10-membered heterocyclic ring. The specific examples include pyrrolidine, piperidine and tetrahydrofuran.

The "aliphatic carbocyclic or heterocyclic ring" in the optionally substituted aliphatic carbocyclic or heterocyclic ring is preferably a 4- to 10-membered ring, and more preferably a 5- to 8-membered ring.

The "aromatic ring" in the optionally substituted aromatic ring is, for example, a 5- to 12-membered aromatic ring. The specific examples include benzene and naphthalene.

The "hetero-aromatic ring" in the optionally substituted hetero-aromatic ring is, for example, a 5- to 12-membered aromatic ring. The specific examples include furan, pyrrole, thiophene, oxazole, imidazole, thiazole, pyridine, pyridazine, pyrimidine and pyrazine.

The "aromatic or hetero-aromatic ring" in the optionally substituted aromatic or hetero-aromatic ring is preferably a 5- to 12-membered ring, and more preferably a 6- to 10-membered ring.

Examples of the substituting group in the optionally substituted aliphatic carbocyclic or heterocyclic ring and in the optionally substituted aromatic or hetero-aromatic ring are the same as those of the substituting group in the "straight or branched alkyl group" described above. The number of the substituting groups in the optionally substituted aliphatic carbocyclic or heterocyclic ring and in the optionally substituted aromatic or hetero-aromatic ring is for example 1 to 4, and preferably 1 to 2.

Preferable examples of the ring include cyclic ketones having, as a basic skeleton, α-tetralone, β-tetralone, indanone, 1-benzosuberone, 2-benzosuberone, 3-chromanone, 4-chromanone, β-coumaranone, dihydroquinolinone, dihydroisoquinolinone, thiochromanone or the like; and compounds in which the foregoing cyclic ketone is substituted at any appropriate position by the above-listed substituent. More preferred are α-tetralone, β-tetralone and compounds in which α- or β-tetralone is substituted at any appropriate position by the above-listed substituent.

The ketone used as the starting material in the present invention is preferably a condensed ring compound which (i) has a carbonyl group, (ii) optionally has a substituting group other than a carbonyl group, and (iii) is constituted of a 4- to 10-membered aliphatic or aromatic ring and an optionally substituted 5- to 12-membered aromatic or hetero-aromatic ring, each ring optionally containing one or more atoms which may be the same or different and are selected from an oxygen atom, an optionally substituted nitrogen atom and a sulfur atom.

The carbonyl group may be located at any position of the 4- to 10-membered aliphatic or aromatic ring. Optionally, the carbonyl group may be adjacent to the position for the condensation of the 4- to 10-membered aliphatic or aromatic ring and the 5- to 12-membered aromatic or hetero-aromatic ring.

Examples of the substituting group other than a carbonyl group in the above condensed ring compound are the same as those of the substituting group in the "straight or branched alkyl group" described above.

As a constituent of the condensed ring, the 4- to 10-membered aliphatic ring optionally containing one or more atoms which may be the same or different and are selected from an oxygen atom, an optionally substituted nitrogen atom and a sulfur atom is, for example, cyclobutane, cyclopentane, cyclohexane, cycloheptane, cyclooctane, cyclononane, cyclodecane, cyclohexene, pyrrolidine, piperidine, tetrahydrofuran or the like.

As another constituent of the condensed ring, the 5- to 12-membered aromatic or hetero-aromatic ring optionally containing one or more atoms which may be the same or different and are selected from an oxygen atom, an optionally substituted nitrogen atom and a sulfur atom is, for example, benzene, naphthalene, furan, pyrrole, thiophene, oxazole, imidazole, thiazole, pyridine, pyridazine, pyrimidine, pyrazine or the like.

Examples of the substituting group in the optionally substituted nitrogen atom are the same as those of the substituting group in the "straight or branched alkyl group" described above.

Examples of the substituting group in the constituents of the condensed ring, i.e., the 4- to 10-membered aliphatic or aromatic ring and the 5- to 12-membered aromatic or hetero-aromatic ring, are the same as those of the substituting group in the "straight or branched alkyl group" described above.

Preferable examples of the condensed ring compound include cyclic ketones having, as a basic skeleton, α-tetralone, β-tetralone, indanone, 1-benzosuberone, 2-benzosuberone, 3-chromanone, 4-chromanone, β-coumaranone, dihydroquinolinone, dihydroisoquinolinone or thiochromanone; and compounds in which the foregoing cyclic ketone is substituted at any appropriate position by the above-listed substituent. More preferred are α-tetralone, β-tetralone and compounds in which α- or β-tetralone is substituted at any appropriate position by the above-listed substituent.

<Hydrogen Donor Compound>

In the production method of the present invention, the ketone is reduced by reacting with a hydrogen donor compound. The hydrogen donor compound used for the present invention is not particularly limited and the examples include reducing compounds such as formic acid and 2-propanol; and salts thereof such as sodium formate, potassium formate and ammonium formate. For high enantiomeric excess of the product, formic acid, a salt thereof or a mixture of formic acid and its salt is preferred because the use of this compound allows acidic conditions to be maintained throughout the reaction. The use of sodium formate, potassium formate or ammonium formate alone makes the reaction mixture basic and thus may cause base-catalyzed racemization of the chiral prolinamide compound, which is the ligand of the iridium(III) complex used for the reaction, possibly leading to low enantiomeric excess. For that reason, in the case where sodium formate, potassium formate, ammonium formate or the like is used as a hydrogen donor compound in an aqueous solvent, it is preferable to carry out the reaction in the presence of an acidic buffer solution prepared from, for example, sodium acetate and acetic acid.

The amount of the hydrogen donor compound used for the reaction is usually about 1 to 40 mol, and preferably about 2 to 20 mol per mole of compound [I].

The hydrogen donor compound is preferably used together with a weak base. Preferable examples of the weak base include tertiary amines such as triethylamine, trimethylamine, tributylamine and N-methylmorpholine; alkali metal hydrogen carbonates such as sodium hydrogen carbonate and potassium hydrogen carbonate; and alkali earth metal carbonates such as calcium carbonate and magnesium carbonate, and more preferred is triethylamine. It is also preferable to use an azeotropic mixture of the hydrogen donor compound and a tertiary amine, and for example, an azeotropic mixture of formic acid and triethylamine (the molar ratio of formic acid/triethylamine=5/2) etc. can also be used without any problem.

In the case where the iridium(III) compound as a starting material is a dimer, the amount of the base used for the reaction is usually about 2 to 3 mol, and preferably about 2 to 2.2 mol per mole of the dimer.

<Solvent>

Examples of the solvent used in the production method of the present invention include acetonitrile, ethyl acetate, isopropyl acetate, N,N-dimethylformamide, tetrahydrofuran, dimethoxyethane, dichloromethane, alcohols such as methanol, ethanol, 2-propanol and ethylene glycol, and mixed solvents of water and the foregoing. The amount of the solvent used for the reaction is usually about 2 to 200 L, and preferably about 5 to 100 L per kilogram of the ketone.

The above-mentioned mixture of formic acid and triethylamine can be used as the solvent as well as the hydrogen donor compound. In the case where the mixture of formic acid and triethylamine is used as the solvent as well as the hydrogen donor compound, the amount of formic acid used for the reaction is usually about 1 to 80 mol, and preferably about 1 to 40 mol per mole of the ketone. The amount of triethylamine used for the reaction is usually about 0.1 to 1 mol, and preferably about 0.2 to 0.7 mol per mole of formic acid.

<Reaction>

In a preferred embodiment, the reducing reaction in the production method of the present invention is carried out as follows: to a solution of compound [I], an iridium(III) complex having a chiral prolinamide compound as a ligand is added and dissolved, and then to the solution, a hydrogen donor compound is added.

The reaction temperature of this reaction is usually −70° C. or higher, and preferably about −30 to 40° C.

After the completion of the reaction, the desired optically active alcohol can be obtained by known processes such as extraction, concentration, filtration and washing. If needed, purification procedures such as crystallization, recrystallization, distillation and column chromatography may be further employed to obtain the optically active alcohol in a higher purity.

<Product>

The optically active alcohol as the product in the production method of the present invention is not particularly limited and may be any compound having a hydroxyl group and a structure corresponding to the starting material ketone.

The optically active alcohol as the product in the production method of the present invention is preferably a compound represented by formula [II]:

(wherein $R^1$ and $R^2$ are as defined in formula [I], and the symbol * indicates that the carbon atom is a chiral center).

The definitions and examples of $R^1$ and $R^2$ are the same as those described in formula [I].

The optically active alcohol as the product in the production method of the present invention preferably has an optionally substituted aliphatic carbocyclic or heterocyclic ring which constitutes a condensed ring in combination with an optionally substituted aromatic or hetero-aromatic ring.

More preferably, the optically active alcohol as the product in the production method of the present invention is a condensed ring compound which (i) has a hydroxyl group, (ii) optionally has a substituting group other than a hydroxyl group, and (iii) is constituted of a 4- to 10-membered aliphatic ring and an optionally substituted 5- to 12-membered aromatic or hetero-aromatic ring, each ring optionally containing one or more atoms which may be the same or different and are selected from an oxygen atom, an optionally substituted nitrogen atom and a sulfur atom.

Preferable examples of the optically active alcohol include cyclic alcohols having, as a basic skeleton, α-tetralol, β-tetralol, indanol, 1-benzosuberol, 2-benzosuberol, 3-chromanol, 4-chromanol, β-coumaranol, dihydroquinolinol, dihydroisoquinolinol or thiochromanol; and compounds in which the foregoing cyclic alcohol is substituted at any appropriate position by the above-listed substituent. More preferred are α-tetralol, β-tetralol and compounds in which α- or β-tetralol is substituted at any appropriate position by the above-listed substituent.

According to the production method of the present invention, regardless of the structure of starting material ketones, the production of optically active alcohols in high optical yields can be generally attained. That is, optically active alcohols can be produced from various kinds of ketones in an industrially advantageous manner with the use of an iridium (III) complex having, as a ligand, a chiral prolinamide compound represented by formula [III].

The optically active alcohol produced by the production method of the present invention can be used as a synthetic raw material for the production of pharmaceuticals, agrochemicals, liquid crystal materials, fine chemicals, etc.

<Catalyst>

The catalyst used for the present invention is not particularly limited as long as it is an iridium(III) complex having a chiral prolinamide compound as a ligand.

<Catalyst Preparation>
<Iridium(III) Compound>

Examples of the iridium(III) compound used for the preparation of the catalyst include pentamethylcyclopentadienyl iridium(III) chloride dimer, acetylacetonato iridium(III) and tris(norbornadiene)(acetylacetonato)iridium(III), and particularly preferred is pentamethylcyclopentadienyl iridium (III) chloride dimer.

<Chiral Prolinamide Compound>

Examples of the chiral prolinamide compound include a compound represented by formula [III]:

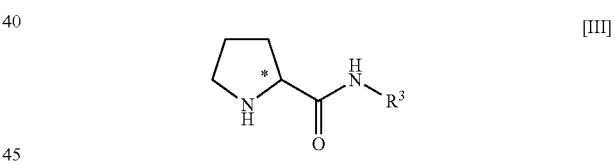

(wherein $R^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol * indicates that the carbon atom is a chiral center).

Examples of the prolinamide compound represented by formula [III] include, in addition to prolinamide itself, N-substituted amide such as N-alkyl amide, N-cycloalkyl amide, N-aryl amide, N-heteroaryl amide, N-aralkyl amide and N-heteroarylalkyl amide. These substituting groups are examples of $R^3$ and may also have a substituting group (hereinafter also called a substituent).

Examples of the "alkyl," "heteroaryl," "aralkyl" and "heteroarylalkyl" groups in the N-alkyl amide are the same as those of the corresponding groups represented by $R^1$ and $R^2$ described above.

Examples of the substituting group in the "alkyl," "heteroaryl," "aralkyl" and "heteroarylalkyl" groups in the N-alkyl amide are the same as those of substituting group (A) described above.

The chiral prolinamide compound is preferably (R)-2-pyrrolidinecarboxamide or (S)-2-pyrrolidinecarboxamide, or (R)-proline heteroaryl amide or (S)-proline heteroaryl amide, and more preferably (R)-2-pyrrolidinecarboxamide or (S)-2-pyrrolidinecarboxamide. A preferable chiral proline heteroaryl amide compound is (R)—N-(6-quinolinyl)-2-pyrrolidinecarboxamide or (S)—N-(6-quinolinyl)-2-pyrrolidinecarboxamide, (R)—N-(2-methoxy-3-dibenzofuranyl)-2-pyrrolidinecarboxamide or (S)—N-(2-methoxy-3-dibenzofuranyl)-2-pyrrolidinecarboxamide, or the like because the use of these compounds as the ligand of the iridium complex catalyst for the reducing reaction is advantageous in terms of the optical purity of the product and the reactivity.

The amount of the iridium(III) complex having a chiral prolinamide compound as a ligand used for the reaction is usually about 0.1 to 10 mol %, and preferably about 0.2 to 5 mol % relative to the ketone.

<Base Used for Catalyst Preparation>

The base used for the catalyst preparation is preferably a weak base, more preferably a tertiary amine such as triethylamine, trimethylamine, tributylamine and N-methylmorpholine; an alkali metal hydrogen carbonate such as sodium hydrogen carbonate and potassium hydrogen carbonate; or an alkali earth metal carbonate such as calcium carbonate and magnesium carbonate, and particularly preferably triethylamine. Strong bases including alkali metal hydroxides, such as sodium hydroxide and potassium hydroxide, and sodium methoxide, are not preferable for use in the catalyst preparation because strong bases cause epimerization of the resulting prolinamide complex, which leads to a reduced optical purity.

In the case where the iridium(III) compound as a starting material is a dimer, the amount of the base used for the catalyst preparation is usually about 2 to 3 mol, and preferably about 2 to 2.2 mol per mole of the dimer.

<Solvent Used for Catalyst Preparation>

The solvent used for the catalyst preparation is preferably an organic solvent. Examples of the organic solvent include aliphatic hydrocarbons (for example, pentane, hexane, heptane, octane, cyclohexane, etc.); aromatic hydrocarbons (for example, benzene, toluene, xylene, etc.); halogenated hydrocarbons (for example, dichloromethane, 1,2-dichloroethane, chloroform, carbon tetrachloride, o-dichlorobenzene, etc.); alcohols (for example, methanol, ethanol, isopropyl alcohol, tert-butyl alcohol, tert-amyl alcohol, etc.); ethers (for example, dimethyl ether, ethylmethyl ether, diethyl ether, diisopropyl ether, diglyme, tert-butyl methyl ether, dimethoxyethane, ethylene glycol diethyl ether, tetrahydrofuran, 1,4-dioxane, etc.); amides (for example, N,N-dimethylformamide, N,N-dimethylacetamide, N-methylpyrrolidone, etc.); sulfoxides (for example, dimethyl sulfoxide etc.); nitriles (for example, acetonitrile, propionitrile, benzonitrile, etc.); ketones (for example, acetone, methyl ethyl ketone, methyl isobutyl ketone, etc.); and ester compounds (for example, methyl acetate, ethyl acetate, etc.). In the case where highly water-miscible alcohols, ethers, amides, sulfoxides, nitriles, ketones or esters are used as the solvent, the water content of the solvent may be up to about 50%. Among the above examples, more preferred is methanol, water-containing methanol, ethanol, water-containing ethanol, methylene chloride, ethyl acetate or acetonitrile.

<Reaction in Catalyst Preparation>

The catalyst used for the present invention, i.e., the iridium (III) complex having a chiral prolinamide compound as a ligand can be prepared by dissolving a chiral prolinamide compound in a solvent, adding an iridium(III) compound and a base (for example, triethylamine etc.) to the solution, and stirring the mixture preferably at room temperature usually for 10 minutes to 20 hours.

<Iridium(III) Complex Having a Chiral Prolinamide Compound as a Ligand>

As the catalyst used in the production method of the present invention, the iridium (III) complex having a chiral prolinamide compound as a ligand may be any complex formed from a chiral prolinamide compound and a trivalent iridium(III) compound.

The catalyst used in the production method of the present invention is preferably a complex formed from a chiral prolinamide compound represented by formula [III]:

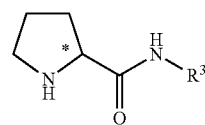

[III]

(wherein $R^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol * indicates that the carbon atom is a chiral center) and
a trivalent iridium compound. Hereinafter, this complex is also called an iridium(III) complex.

Examples of the iridium(III) complex having a chiral prolinamide compound as a ligand include an (R)- or (S)-chloro [(1,2,3,4,5-η)-pentamethyl-2,4-cyclopentadien-1-yl] [N-(2-methoxy-3-dibenzofuranyl)-2-pyrrolidinecarboxamidato-κN1,κN2]iridium(III) complex, an (R)- or (S)-chloro[(1,2,3,4,5-η)-pentamethyl-2,4-cyclopentadien-1-yl] (N-6-quinolinyl-2-pyrrolidinecarboxamidato-κN1, κN2)iridium (III) complex, and an (R)- or (S)-chloro[(1,2,3,4,5-η)-pentamethyl-2,4-cyclopentadien-1-yl] (2-pyrrolidinecarboxamidato-κN1,κN2)iridium(III) complex.

After the iridium(III) complex having a chiral prolinamide compound as a ligand is prepared, the resulting catalyst-containing mixture can be directly used as a catalyst for asymmetric reduction in the production method of the present invention, but more preferably, an crystalline iridium(III) complex isolated and purified from the catalyst-containing mixture is used for asymmetric reduction. This is because, when the isolated and purified iridium(III) III) complex in a crystalline form is used as a catalyst for asymmetric reduction, the chemical yield and the enantiomeric excess of the product will be higher than those in the case where the catalyst-containing mixture is directly used.

The reason for this is that, during the preparation of the catalyst and the subsequent period when the resulting catalyst-containing mixture is left unused, the base in the catalyst-containing mixture causes partial epimerization of the iridium(III) complex, which results in a reduced optical purity of the catalyst. Therefore, in the case where the catalyst-containing mixture is directly used, it should be used immediately after the preparation. In contrast, in the case where the iridium(III) complex is isolated and purified from the catalyst-containing mixture, the base responsible for epimerization and the epimerized product (epimer) can be eliminated, and thus the iridium(III) complex can be obtained in a crystalline form with high optical purity and good preservation stability.

Examples of the isolation and purification method include the following. In one example, the resulting iridium(III) complex is isolated by, for example, concentration of the reaction mixture and subsequently purified by a known recrystallization or reprecipitation method. In another example, complex formation is performed in a solvent that allows highly efficient purification, and after a purification process, the resulting precipitate as the main product is collected by filtration, washed and dried. By use of any of these methods, the iridium (III) complex can be easily obtained in a crystalline form as a chemically and optically pure product.

The isolated and purified iridium(III) complex in a crystalline form is highly stable, the chemical and optical purities thereof stay constant for a long period, and thus the complex can be preserved at room temperature for a long period. With the use of this complex as a catalyst for asymmetric reduction, the reduction product can be obtained with high chemical yield and enantiomeric excess.

EXAMPLES

Hereinafter, the present invention will be illustrated in detail by the examples shown below, but is not limited thereto.
<Measurement Methods>

Nuclear magnetic resonance (NMR) spectra were recorded on Gemini-200 (manufactured by Varian Medical Systems, Inc.). The internal standard used was TMS (tetramethylsilane), the solvent used was $CDCl_3$ or $CD_3OD$, and the measurement was performed at room temperature. The measured values were reported in $\delta$ (ppm).

High performance liquid chromatography (HPLC) was performed with LC10A (manufactured by Shimadzu Corporation). Optical purities were determined from the difference in the retention time obtained by HPLC.

Specific rotations were measured with P-1020 (manufactured by JASCO Corporation).

The solvents and reagents used in the reactions described below are commercial products if not otherwise specified.

Example 1

In 30 ml of methanol, 529 mg of 7-methoxy-β-tetralone was dissolved, and 57 mg of (S)-chloro[(1,2,3,4,5-η)-pentamethyl-2,4-cyclopentadien-1-yl] (2-pyrrolidinecarboxamidato-κN1,κN2)iridium(III) was added. After the solution was cooled to −10° C., 7.5 ml of a mixture of formic acid/triethylamine (molar ratio: 5/2) was added dropwise, and the resulting mixture was continuously stirred at the same temperature for 2 days. Then, the reaction was completed. The reaction mixture was concentrated in vacuo and extracted with methylene chloride. After the extract was basified with an aqueous sodium carbonate solution, the resulting layers were separated. The organic layer was washed with water and concentrated to give 480 mg of 7-methoxy-2-tetralol as an oil.

By the analysis using a chiral column (CHIRALPAK AD-H; manufactured by Daicel Chemical Industries, Ltd., eluent: n-hexane/2-propanol=95/5), the resulting compound was identified as (R)-7-methoxy-2-tetralol, and the optical purity of the desired compound (R-enantiomer) was found to be 92.0% ee.
<Results>

Specific rotation: $[\alpha]_D^{20}$ +45.6 (c=1.24, $CHCl_3$)
$^1$H-NMR (200 MHz, $CDCl_3$): δ 1.70-1.89 (1H, m, one of 3-$H_2$), 1.85 (1H, s, OH), 1.96-2.11 (1H, m, one of 3-$H_2$), 2.66-3.11 (4H, m, 1-$H_2$ and 4-$H_2$), 3.77 (3H, s, OMe), 4.07-4.20 (1H, m, 2-H), 6.61 (1H, d, J=2.7 Hz, ArH), 6.70 (1H, dd, J=8.4, 2.7 Hz, ArH), 7.00 (1H, d, J=8.4 Hz, ArH).

$^{13}$C-NMR (50.3 MHz, $CDCl_3$): δ26.1 ($CH_2$), 31.7 ($CH_2$), 38.6 ($CH_2$), 55.2 (OMe), 67.2 (2-C), 112.4 (ArCH), 114.0 (ArCH), 127.7 (quaternary ArC), 129.4 (ArCH), 135.4 (quaternary ArC), 157.7 (quaternary ArC).

Example 2

In 2 ml of methanol, 292 mg of β-tetralone was dissolved, and 38 mg of (S)-chloro[(1,2,3,4,5-η)-pentamethyl-2,4-cyclopentadien-1-yl] (2-pyrrolidinecarboxamidato-κN1,κN2) iridium(III) was added. After the solution was cooled to −10° C., 5.0 ml of a mixture of formic acid/triethylamine (molar ratio: 5/2) was added dropwise, and the resulting mixture was continuously stirred at the same temperature for 2 days. Then, the reaction was completed. The reaction mixture was concentrated in vacuo and extracted with methylene chloride. After the extract was basified with an aqueous sodium carbonate solution, the resulting layers were separated. The organic layer was washed with water and concentrated to give 268 mg of 2-tetralol as an oil.

By the analysis using a chiral column (CHIRALPAK AD-H; manufactured by Daicel Chemical Industries, Ltd., eluent: n-hexane/2-propanol=50/1), the resulting compound was identified as (R)-2-tetralol, and the optical purity of the desired compound (R-enantiomer) was found to be 89.6% ee.
<Results>

Specific rotation: $[\alpha]_D^{20}$ +57.6 (c=1.07, $CHCl_3$)
$^1$H-NMR (200 MHz, $CDCl_3$): δ 1.71-1.90 (1H, m, one of 3-$H_2$), 1.85 (1H, s, OH), 1.97-2.12 (1H, m, one of 3-$H_2$), 2.68-3.14 (4H, m, 1-$H_2$ and 4-$H_2$), 4.08-4.21 (1H, m, 2-H), 7.05-7.15 (4H, m, ArH).

$^{13}$C-NMR (50.3 MHz, $CDCl_3$): δ26.9 ($CH_2$), 31.4 ($CH_2$), 38.4 ($CH_2$). 67.2 (2-C), 125.8 (ArCH), 125.9 (ArCH), 128.6 (ArCH), 129.5 (ArCH), 134.2 (quaternary ArC), 135.6 (quaternary ArC).

Example 3

In 20 ml of methanol, 352 mg of 7-methoxy-α-tetralone was dissolved, and 38 mg of (S)-chloro[(1,2,3,4,5-η)-pentamethyl-2,4-cyclopentadien-1-yl] (2-pyrrolidinecarboxamidato-κN1,κN2)iridium(III) was added. After the solution was cooled to −10° C., 5.0 ml of a mixture of formic acid/triethylamine (molar ratio: 5/2) was added dropwise, and the resulting mixture was continuously stirred at the same temperature for 2 days. Then, the reaction was completed. The reaction mixture was concentrated in vacuo and extracted with methylene chloride. After the extract was basified with an aqueous sodium carbonate solution, the resulting layers were separated. The organic layer was washed with water and concentrated to give 334 mg of 7-methoxy-α-tetralol as an oil.

By the analysis using a chiral column (CHIRALPAK AD-H; manufactured by Daicel Chemical Industries, Ltd., eluent: n-hexane/2-propanol=50/1), the resulting compound was identified as (R)-7-methoxy-α-tetralol, and the optical purity of the desired compound (R-enantiomer) was found to be 98.1% ee.
<Results>

Specific rotation: $[\alpha]_D^{20}$ −46.8 (c=1.33, $CHCl_3$)
$^1$H-NMR (200 MHz, $CDCl_3$): δ 1.68-2.04 (4H, m, 2-$H_2$ and 3-$H_2$), 1.84 (1H, s, OH), 2.56-2.83 (2H, m, 4-$H_2$), 3.79 (3H, s, OMe), 4.72 (1H, dd, J=5.5, 4.6 Hz, 1-H), 6.77 (1H, dd, J=8.2, 2.7 Hz, ArH), 6.98 (1H, d, J=2.7 Hz, ArH), 7.01 (1H, d, J=8.2 Hz, ArH).

$^{13}$C-NMR (50.3 MHz, $CDCl_3$): δ19.2 ($CH_2$), 28.4 ($CH_2$), 32.4 ($CH_2$), 55.3 (OMe), 68.4 (1-C), 112.6 (ArCH), 114.3

(ArCH), 129.1 (quaternary ArC), 129.9 (ArCH), 139.8 (quaternary ArC), 157.9 (quaternary ArC).

Example 4

In 40 ml of methanol, 296 mg of 4-chromanone was dissolved, and 38 mg of (S)-chloro[(1,2,3,4,5-η)-pentamethyl-2,4-cyclopentadien-1-yl] (2-pyrrolidinecarboxamidato-κN1, κN2)iridium(III) was added. After the solution was cooled to −20° C., 4.0 ml of a mixture of formic acid/triethylamine (molar ratio: 5/2) was added dropwise, and the resulting mixture was continuously stirred at the same temperature for 2 days. Then, the reaction was completed. The reaction mixture was concentrated in vacuo and extracted with methylene chloride. After the extract was basified with an aqueous sodium carbonate solution, the resulting layers were separated. The organic layer was washed with water and concentrated. The resulting oil was purified by silica gel column chromatography to give 260 mg of a colorless crystal.

By the analysis of this product using a chiral column (CHIRALPAKIB; manufactured by Daicel Chemical Industries, Ltd., n-hexane/2-propanol=95/5), the optical purity was found to be 99.0% ee. This product was (R)-4-chromanol.
<Results>
Specific rotation: $[\alpha]_D^{20}$ 72.7 (c=0.5, EtOH)
$^1$H-NMR (200 MHz, CDCl$_3$): δ 1.93-2.19 (3H, m, 3-H$_2$ and OH), 4.19-4.33 (2H, m, 2-H$_2$), 4.75 (1H, br t, J=3.9 Hz, 4-H), 6.83 (1H, dd, J=8.2, 1.3 Hz, 8-H), 6.91 (1H, td, J=7.5, 1.3 Hz, 6-H), 7.20 (1H, ddd, J=8.2, 7.5, 1.6 Hz, 7-H), 7.30 (1H, dd, J=7.5, 1.6 Hz, 5-H).
$^{13}$C-NMR (50.3 MHz, CDCl$_3$): δ30.8 (3-C), 61.9 (2-C), 63.2 (4-C), 117.1 (ArCH), 120.6 (ArCH), 124.3 (quaternary ArC), 129.6 (overlapped, 2×ArCH), 154.6 (quaternary ArC).

Example 5

In 40 ml of methanol, 373 mg of 2-benzylidenecyclohexanone was dissolved, and 38 mg of (S)-chloro[(1,2,3,4,5-η)-pentamethyl-2,4-cyclopentadien-1-yl] (2-pyrrolidinecarboxamidato-κN1,κN2)iridium(III) was added. After the solution was cooled to −20° C., 4.0 ml of a mixture of formic acid/triethylamine (molar ratio: 5/2) was added dropwise, and the resulting mixture was continuously stirred at the same temperature for 2 days. Then, the reaction was completed. The reaction mixture was concentrated in vacuo and extracted with methylene chloride. After the extract was basified with an aqueous sodium carbonate solution, the resulting layers were separated. The organic layer was washed with water and concentrated. The resulting oil was purified by silica gel column chromatography to give 273 mg of a colorless crystal.

By the analysis of this product using a chiral column (CHIRALPAKIB; manufactured by Daicel Chemical Industries, Ltd., n-hexane/2-propanol=95/5), the optical purity was found to be 85.3% ee. This product was (E)-(1S)-2-benzylidenecyclohexanol.
<Results>
Specific rotation: $[\alpha]_D^{20}$ −33.0 (c=0.5, CHCl$_3$)
$^1$H-NMR (200 MHz, CDCl$_3$): δ 1.38-1.71 (4H, m, 2×CH$_2$), 1.77-2.19 (4H, m, 3H of 2×CH$_2$ and OH), 2.65-2.79 (1H, m, one of CH$_2$), 4.23 (1H, ddd, J=8.1, 4.0, 1.3 Hz, 1-H), 6.52 (1H, br s, benzylic H), 7.16-7.25 (3H, m, ArH), 7.27-7.39 (2H, m, ArH).
$^{13}$C-NMR (50.3 MHz, CDCl$_3$): δ23.2 (CH$_2$), 27.0 (CH$_2$), 27.3 (CH$_2$), 36.5 (CH$_2$), 73.7 (1-C), 120.8 (ArCH), 126.2 (ArCH), 128.1 (ArCH), 128.9 (ArCH), 137.7 (quaternary ArC), 144.3 (quaternary ArC).

INDUSTRIAL APPLICABILITY

According to the present invention, ordinary ketones can be used without any structural limitation as a starting material for the production of optically active alcohols, and a wide variety of optically active alcohols can be provided in high optical and chemical purities with the use of the starting material and an inexpensive complex catalyst. Therefore, the present invention is industrially useful.

The invention claimed is:
1. A method for producing optically active alcohols, comprising reducing a ketone in the presence of an iridium(III) complex having a chiral prolinamide compound as a ligand
wherein the ketone is a compound represented by formula [I]:

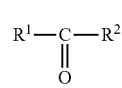

(wherein R$^1$ and R$^2$ are different from each other, and each represent an optionally substituted straight or branched alkyl group, an optionally substituted cycloalkyl group, an optionally substituted aryl group, an optionally substituted heteroaryl group, an optionally substituted aralkyl group, an optionally substituted heteroarylalkyl group, an optionally substituted alkenyl group or an optionally substituted alkynyl group, and
R$^1$ and R$^2$ are bound to each other at any appropriate position to form a ring, the ring optionally containing one or more atoms which may be the same or different and are selected from an oxygen atom, an optionally substituted nitrogen atom and a sulfur atom),
wherein the ring is a condensed ring of an optionally substituted aliphatic carbocyclic or heterocyclic ring and an optionally substituted aromatic or hetero-aromatic ring,
wherein the chiral prolinamide compound is a compound represented by formula [III]:

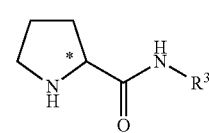

(wherein R$^3$ represents a hydrogen atom or an optionally substituted heteroaryl group, and the symbol * indicates that the carbon atom is a chiral center).
2. The method according to claim 1, wherein the optically active alcohol is a compound represented by formula [II]:

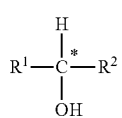

(wherein R$^1$ and R$^2$ are as defined in formula [I], and the symbol * indicates that the carbon atom is a chiral center).

3. The method according to claim 1, wherein the chiral prolinamide compound is (R)-proline heteroaryl amide or (S)-proline heteroaryl amide.

4. The method according to claim 1, wherein the chiral prolinamide compound is (R)—N-(6-quinolinyl)-2-pyrrolidinecarboxamide or (S)—N-(6-quinolinyl)-2-pyrrolidinecarboxamide.

5. The method according to claim 1, wherein the chiral prolinamide compound is (R)—N-(2-methoxy-3-dibenzofuranyl)-2-pyrrolidinecarboxamide or (S)—N-(2-methoxy-3-dibenzofuranyl)-2-pyrrolidinecarboxamide.

6. The method according to claim 1, wherein the chiral prolinamide compound is (R)-2-pyrrolidinecarboxamide or (S)-2-pyrrolidinecarboxamide.

7. The method according to claim 1, wherein the iridium (III) complex having a chiral prolinamide compound as a ligand is an (R)- or (S)-chloro[(1,2,3,4,5-η)-pentamethyl-2,4-cyclopentadien-1-yl][N-(2-methoxy-3-dibenzofuranyl)-2-pyrrolidinecarboxamidato-κN1,κN2]iridium(III) catalyst, or an (R)- or (S)-chloro[(1,2,3,4,5-η)-pentamethyl-2,4-cyclopentadien-1-yl](N-6-quinolinyl-2-pyrrolidinecarboxamidato-κN1,κN2)iridium(III) catalyst.

8. The method according to claim 1, wherein the iridium (III) complex having a chiral prolinamide compound as a ligand is an (R)- or (S)-chloro [(1,2,3,4,5-η)-pentamethyl-2,4-cyclopentadien-1-yl] (2-pyrrolidinecarboxamidato-κN1,κN2)iridium(III) catalyst.

9. The method according to claim 1, wherein the iridium (III) complex having a chiral prolinamide compound as a ligand is crystalline.

10. The method according to claim 1, wherein the ketone is reduced by reacting with a hydrogen donor compound.

11. The method according to claim 10, wherein the hydrogen donor compound is formic acid or a salt thereof.

12. A method for producing an optically active alcohol, comprising reducing a ketone in the presence of an iridium (III) complex having a chiral prolinamide compound as a ligand, wherein the chiral prolinamide compound is (R)—N-(6-quinolinyl)-2-pyrrolidinecarboxamide, (S)—N-(6-quinolinyl)-2-pyrrolidinecarboxamide, (R)—N-(2-methoxy-3-dibenzofuranyl)-2-pyrrolidinecarboxamide or (S)—N-(2-methoxy-3-dibenzofuranyl)-2-pyrrolidinecarboxamide.

13. The method according to claim 12, wherein the ketone is a compound represented by formula [I]:

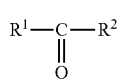

[I]

(wherein $R^1$ and $R^2$ are different from each other, and each represent an optionally substituted straight or branched alkyl group, an optionally substituted cycloalkyl group, an optionally substituted aryl group, an optionally substituted heteroaryl group, an optionally substituted aralkyl group, an optionally substituted heteroarylalkyl group, an optionally substituted alkenyl group or an optionally substituted alkynyl group, and $R^1$ and $R^2$ may be bound to each other at any appropriate position to form a ring, the ring optionally containing one or more atoms which may be the same or different and are selected from an oxygen atom, an optionally substituted nitrogen atom and a sulfur atom).

14. The method according to claim 13, wherein the ring is a condensed ring of an optionally substituted aliphatic carbocyclic or heterocyclic ring and an optionally substituted aromatic or hetero-aromatic ring.

15. The method according to claim 12, wherein the optically active alcohol is a compound represented by formula [II]:

wherein $R^1$ and $R^2$ are as defined in formula [I], and the symbol * indicates that the carbon atom is a chiral center.

16. The method according to claim 12, wherein the iridium (III) complex having a chiral prolinamide compound as a ligand is crystalline.

17. The method according to claim 12, wherein the ketone is reduced by reacting with a hydrogen donor compound.

18. The method according to claim 17, wherein the hydrogen donor compound is formic acid or a salt thereof.

19. A method for producing an optically active alcohol, comprising reducing a ketone in the presence of an iridium (III) complex having a chiral prolinamide compound as a ligand, wherein the iridium(III) complex having a chiral prolinamide compound as a ligand is an (R)- or (S)-chloro[(1,2,3,4,5-η)-pentamethyl-2,4-cyclopentadien-1-yl][N-(2-methoxy-3-dibenzofuranyl)-2-pyrrolidinecarboxamidato-κN1,κN2]iridium(III) catalyst, or an (R)- or (S)-chloro[(1,2,3,4,5-η)-pentamethyl-2,4-cyclopentadien-1-yl](N-6-quinolinyl-2-pyrrolidinecarboxamidato-κN1,κN2)iridium(III) catalyst.

20. The method according to claim 19, wherein the ketone is a compound represented by formula [I]:

[I]

(wherein $R^1$ and $R^2$ are different from each other, and each represent an optionally substituted straight or branched alkyl group, an optionally substituted cycloalkyl group, an optionally substituted aryl group, an optionally substituted heteroaryl group, an optionally substituted aralkyl group, an optionally substituted heteroarylalkyl group, an optionally substituted alkenyl group or an optionally substituted alkynyl group, and $R^1$ and $R^2$ may be bound to each other at any appropriate position to form a ring, the ring optionally containing one or more atoms which may be the same or different and are selected from an oxygen atom, an optionally substituted nitrogen atom and a sulfur atom).

21. The method according to claim 20, wherein the ring is a condensed ring of an optionally substituted aliphatic carbocyclic or heterocyclic ring and an optionally substituted aromatic or hetero-aromatic ring.

22. The method according to claim 19, wherein the optically active alcohol is a compound represented by formula [II]:

wherein $R^1$ and $R^2$ are as defined in formula [I], and the symbol * indicates that the carbon atom is a chiral center.

23. The method according to claim 19, wherein the iridium (III) complex having a chiral prolinamide compound as a ligand is crystalline.

24. The method according to claim 19, wherein the ketone is reduced by reacting with a hydrogen donor compound.

25. The method according to claim 24, wherein the hydrogen donor compound is formic acid or a salt thereof.

* * * * *